United States Patent [19]
Hurl, Jr.

[11] Patent Number: 5,296,806
[45] Date of Patent: Mar. 22, 1994

[54] METHOD FOR LOCATING METAL STUDS HIDDEN BEHIND A WALL PARTITION BY USE OF PARTICULATE MAGNETIC MATERIAL

[76] Inventor: Charles J. Hurl, Jr., 846 E. 5th St., South Boston, Mass. 02127

[21] Appl. No.: 965,796

[22] Filed: Oct. 23, 1992

Related U.S. Application Data
[62] Division of Ser. No. 829,949, Feb. 3, 1992, abandoned.

[51] Int. Cl.⁵ .................. G01R 33/00; G01N 27/84
[52] U.S. Cl. ........................ 324/214; 324/67
[58] Field of Search .................. 324/214–215, 324/228–231, 67; 273/443, 448, 456, 239; 434/409, 301

[56] References Cited

U.S. PATENT DOCUMENTS

| | | | |
|---|---|---|---|
| 2,530,564 | 11/1950 | Blaney | 324/214 X |
| 2,723,369 | 11/1955 | Brummett | 324/228 X |
| 3,002,149 | 9/1961 | Christian | 324/228 |
| 3,181,059 | 4/1965 | Mohnkern | 324/214 |
| 3,293,544 | 12/1966 | Seng | 324/214 |
| 3,344,345 | 9/1967 | Molina | 324/215 |
| 3,363,208 | 1/1968 | Balet | 324/228 X |
| 3,432,941 | 3/1969 | Minchom | 434/301 |
| 3,619,313 | 11/1971 | Szuch | 273/239 X |
| 3,755,730 | 8/1973 | Vogelgesang | 324/214 X |
| 5,034,754 | 7/1991 | Taylor et al. | 434/409 X |

FOREIGN PATENT DOCUMENTS

| | | | |
|---|---|---|---|
| 237258 | 11/1969 | U.S.S.R. | 324/214 |
| 0634185 | 11/1978 | U.S.S.R. | 324/214 |
| 502557 | 6/1937 | United Kingdom | 324/214 |

OTHER PUBLICATIONS

Rechen et al, "Use of Iron Filings in a High-Viscosity Medium for Mapping Approximate Magnetic Field Shapes", *The Review of Scientific Instruments*, vol. 28, No. 7, Jul. 1957, p. 584.

*Primary Examiner*—Gerard R. Strecker
*Assistant Examiner*—Warren S. Edmonds
*Attorney, Agent, or Firm*—Herbert L. Gatewood

[57] ABSTRACT

Method for locating metal studs hidden from view by wall board members fastened thereto by screw-type fasteners characterized by a magnetic field of force which attracts particulate magnetic material, by first locating the screw-type fasteners which are hidden from view by spackling compound or other wall surface finishing material. The screw-type fasteners are located by depositing particulate magnetic material on the outer surface of the wall board, the particulate magnetic material being attracted to a screw-type fastener by the magnetic field of force and associating with the head of the fastener in a surrounding manner on the outside surface of the wall board.

8 Claims, 3 Drawing Sheets

METHOD FOR LOCATING METAL STUDS HIDDEN BEHIND A WALL PARTITION BY USE OF PARTICULATE MAGNETIC MATERIAL

This is a division of application Ser. No. 07/829,949 filed Feb. 3, 1992, now abandoned.

BACKGROUND OF THE INVENTION (1) Field of the Invention

This invention relates, in general, to apparatus for, and a method of, locating a metal stud covered over by, and located behind, a wall partition. Further, it relates to apparatus means and a method for locating the metal screws fastening wallboard or the like to metal studs so that such metal screws can be removed and the wallboard then removed essentially intact.

(2) Description of the Prior Art

With more recent building practices, particularly in commercial buildings, it has become somewhat common to provide metal, rather than wooden, studs or upright members in the outer or inner walls of the building. Nevertheless, the use of metal studs is not limited just to commercial buildings. Such members are rather commonly used in new, residential housing construction, and in rehabilitation of older building structures, e.g. in the conversion of schools and other structures to condominiums. In such cases as last mentioned, the old walls may, in fact, be left standing with metal studs and new wall structures merely attached thereto.

Regardless of the building structure involved, once the metal studs are installed, the next step is to install the wall surface members. Thus, to these metal studs are then fastened the panels or wallboard members, e.g. the commonly so-called "dry walls" or other wallboard forming the wall surface. The wallboard members are fastened to the metal studs by a plurality of vertically disposed spaced apart metal screws that are driven through the wallboard member into the upright metal studs which are spaced apart from one another in horizontal disposition along the length of the wall e.g., 16 inches, center stud to center stud. These metal screws are commonly driven into the wall by an electric drill. Nevertheless, the screw heads are generally recessed and taped or spackled over, after which they are hidden, in anticipation of painting or otherwise finishing the walls.

Once a wall is installed and finished, it is sometimes most difficult to locate the concealed metal studs. Nevertheless, it may become necessary from time-to-time for various tradespersons such as carpenters, electricians, cabinet installers, etc., to locate the studs or a particular stud, for various desired purposes. In some cases, it may be desirable to locate all the metal studs behind a particular wall surface and the metal screws holding it so that such a wallboard or the like can be removed intact and later re-installed. Such may be the case where an electrician or plumber may need determine the existence and location of wiring or piping behind a wall surface. Or, when demolishing a building, it may be desirable to remove a wall intact rather than destroying or mutilating it for safety or environmental reasons, e.g., where asbestos is of concern. Even a homeowner may from time-to-time desire to locate a particular stud in a wall to use such as a foundation for mounting objects, e.g. pictures, on the wallboard or other outer surface.

There are, in general, three methods of which I am aware used for locating wall studs. The most fundamental method used is to tap the wall with a hammer at spaced-apart locations horizontally while listening to the sound made, attempting thereby to sense a relatively solid sound which occurs when the hammer is tapped on the wallboard directly in front of a wall stud. This method is mostly trial and error and is sometimes quite frustrating. Although damage to the wall, if any, is generally slight, e.g., dents and scratches, and relatively easily repaired in most cases, a wall stud may be completely missed, depending on the interval or distance apart of the striking locations. Thus, it may be necessary for a person to go over the same wall distance several times, at different tapping intervals, before sensing what appears to be a solid sound. Also, some individual's ears are more attuned to sound differences than others. It is not unusual, moreover, to mistake a solid sound, and to drive a nail into the wallboard only to realize that the stud's location has been missed entirely, or only its edge has been located. When the stud is missed entirely, one must try to locate the stud, once again by tapping at different intervals and a nail must again be driven into the wallboard at chosen locations to determine if the hidden stud has been located.

A second method is to drive a nail through the wallboard at spaced locations along a horizontal line until a wall stud is finally encountered. This method is somewhat akin to the first method and suffers from the same disadvantage. Seldom is one able to choose the correct spacing or interval, in the first place, to locate the stud immediately. Thus, the spacing between "nail holes" may need be adjusted, more or less, until a portion of the stud at least is located. Once a stud is located, its horizontal extents and its center line can then, however, be readily determined. And once the centerline of one stud is located, other studs can then be located provided such are properly located on standard centers. The main disadvantage with this method of locating studs is that it is not only somewhat frustrating but such method necessarily involves physical damage to the wall surface. Each of the nail holes driven into a wallboard not located over a stud must, in general, be plugged, and then painted over, or the wall otherwise finished depending upon the particular wall covering involved. Such a method is not at all desired where the wallboard is papered over. Moreover, although it may be possible to locate a stud by this method, and the method first described, neither is of any help in locating the nails or screws that may have been driven into the wallboard fastening such to the stud.

A third method of locating wall studs involves the use of so-called "stud finders". These devices typically comprise, in general, a magnet supported in a manner to pivot in the presence of magnetic material, e.g. a nail driven through wallboard into a wooden stud. Exemplary of such prior art devices are U.S. Pat. Nos. 2,933,679; 3,293,544; and 3,363,208. None of these patents, however, disclose a device such as is contemplated by my invention. Neither could any of the devices disclosed be used, it is believed, to locate a metal screw driven into a metal stud.

U.S. Pat. No. 2,933,679 discloses a stud finder which makes use of the concept that certain materials of ferrous metal, e.g., nails, screws, or the like are attracted to a magnetic. Thus, in general, the stud finder disclosed comprises an elongated magnet mounted for rotation within a housing. In use, the stud finder is simply grasped by the hand and is moved horizontally along the wall. As a hidden nail holding a wall board to a wooden stud is approached, the pivotally supported elongated magnet will pivot and will align itself with the embedded nail. Although such a device might be helpful in locating a metal stud itself, as desired in part herein, the device will not, however, be found useful to locate the metal screws driven into a metal stud. This is because the magnet in the stud finder device will, it is believed, be attracted to the stud itself, not being able to distinguish between the metal stud and the metal screws located therein. Thus, locating the metal screws in a metal stud for removing such and the wallboard intact would still be largely a hit-and-miss operation. Moreover, the device disclosed in that patent includes a magnet searching, in a sense, for metal attracted thereby whereas my invention does not operate in such a fashion. As disclosed more fully later, my invention instead provides metal particles that are attracted to the metal screws located in the metal stud, and as such the metal screws act like magnets.

In U.S. Pat. No. 3,293,544, there is disclosed a nail detector using metallic particles. The nail detector comprises, in general, a spool located within a case, having a transparent outer face. The spool has a centrally disposed opening which extends from adjacent the transparent outer face to the rear face of the case which is in contact with a wall. A coil is provided upon the outer circumference of the spool connected to a source of electric current. When the coil is electrically energized it creates a magnetic field and magnetically exercises a plurality of iron filings seen through the transparent face. The case is moved along the wall while the iron filings are energized. As a result, when the opening in the spool passes over a hidden nail head, the iron filings will have a tendency to collect over the nail head, due to the nail being magnetized. The inner wall of the spool surrounding the opening, however, and at the location of the nail head, will permit the iron filings only to gather around the opening. When a nail head is so located, a pencil is inserted into the opening whereby to make a mark on the wall, at the location of the nail head. Such a device as disclosed in the patent, however, could not be used, it is believed, to locate the metal screws previously driven into a metal stud. It could not distinguish the metal screw from the metal stud.

U.S. Pat. No. 3,363,208 discloses a stud finding device wherein an elongated multiple magnetic sensor provides discernible deflection towards a nail head by one and generally two of a set of vertically mounted magnets pivotally mounted within the sensor. Thus, a plurality of elongated magnets are mounted one above the other, along the length of a U-shaped body member, open at one face. Each magnet is mounted at its top edge for pivotal motion toward the open face, placed against a wall, when a nail is encountered, as the elongated stud finding device is moved along a wall in a vertically upright manner. As the stud finder passes a stud, ordinarily at least two nails will cause a magnet to pivot inwardly toward the nails. This action can be readily detected by feel or observed where the back edge of the body member is of a transparent material. Such a stud finding device is of no use, however, in locating the individual metal screws fastening the wallboard to the metal studs, and which screws are hidden from view behind spackling compound, tape and paint.

SUMMARY OF THE INVENTION

Quite surprisingly, I have discovered that a metal screw when screwed into a metal stud itself becomes a magnet or at least has properties like a magnet and is capable of attracting magnetic materials, e.g. iron filings, to it. Thus, each hidden screw located in a metal stud has what appears to be a magnetic field capable of attracting small particles of iron or other magnetizable material. While I do not wish to be held to this theory, apparently a magnetic force is induced into a metal screw when such is screwed into a metal stud using an electric drill. In any event, I have quite surprisingly discovered such property of attraction exists which makes possible the invention herein disclosed.

In its more basic aspects, my invention comprises means for providing a plurality of magnetic particles, i.e. particles capable of being attracted by a magnet, on and across a wallboard surface in dispersed horizontal fashion. At the same time, such magnetic particles are allowed to fall freely vertically downwardly along the wallboard surface. In so doing, the particles are attracted to the magnetic fields surrounding and associated with the metal screws which are screwed into, and fasten the wallboard to the vertically disposed metal studs. Thus, the magnetic particles in being attracted to the magnetic fields of the metal screws located in a particular stud, will define and determine the location and vertical disposition of any particular stud. And, importantly, the magnetic particles in defining the magnetic field of a particular screw will determine the exact location of a particular metal screw and its center. Thus, by knowing the exact location of the metal screws fastening the wallboard member to the metal studs, these screws can then be more readily located and removed, as desired, and the wallboard member be removed from the studs with little or no damage thereto. Thus, a tradesperson such as a plumber can readily locate hidden plumbing, if need be, without need to cause such damage to a wallboard that necessarily requires replacement with one or more new panels. With my invention the removed wallboard member can be reused, if desired, requiring relatively minor repair of damage.

Of advantage also, with use of the invention disclosed herein, a homeowner or other person can readily locate a metal stud hidden behind a wallboard member, when a more suitable foundation is required for hanging a heavy mirror, picture, or the like on a wall surface.

BRIEF DESCRIPTION OF THE DRAWINGS

Although such novel features believed to be characteristic of the invention disclosed herein are set forth in the claims, the invention and the manner in which it may be carried out may be further understood by reference to the detailed description which follows hereinafter in connection with the accompanying drawings, in which:

DETAILED DESCRIPTION OF THE INVENTION AND THE PREFERRED EMBODIMENTS

Referring now to the drawing there is shown therein, in FIGS. 1-4, a metal stud and screw finding device 10 which comprises a body member 12 defined by a planar, bottom member 14, a top member 16, and planar, spaced-apart vertically disposed side members 18, 20 in parallel disposition to one another. Top member 16 is defined by planar horizontally disposed central portions 22, 24 lying in the same plane which, as can be seen by reference to FIG. 2, terminate at their respective outer ends and join to and are integral with end portions 26, 28 which curve downwardly and terminate in laterally disposed front and rear end edges 30, 32 in the same horizontal plane.

Figure 2:
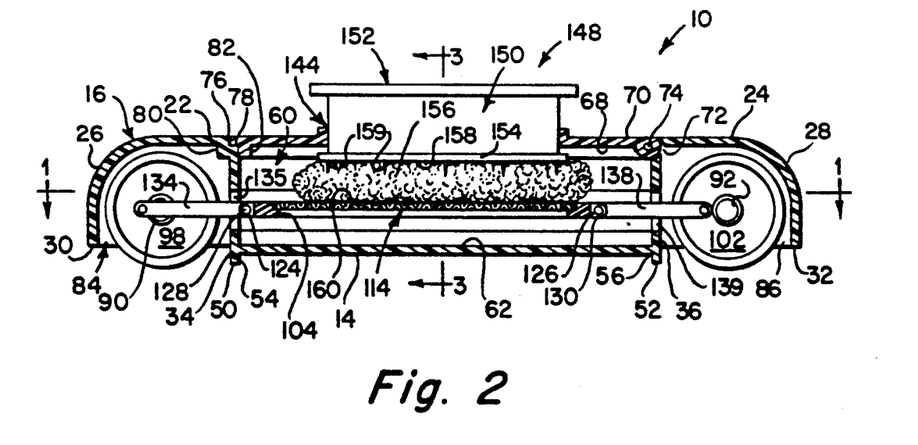
FIG. 2 is a view in longitudinal section taken at secant lines 2—2 in FIG. 1 of apparatus means shown therein for locating the metal studs located behind and hidden from view and supporting a partition wall.
Figure 3:
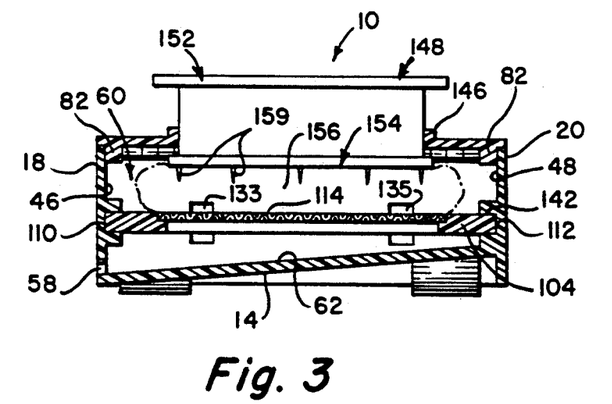
FIG. 3 is a cross-sectional view, taken at secant lines 3—3 in FIG. 2, of the apparatus means of the invention shown in FIGS. 1 and 2.
Figure 4:
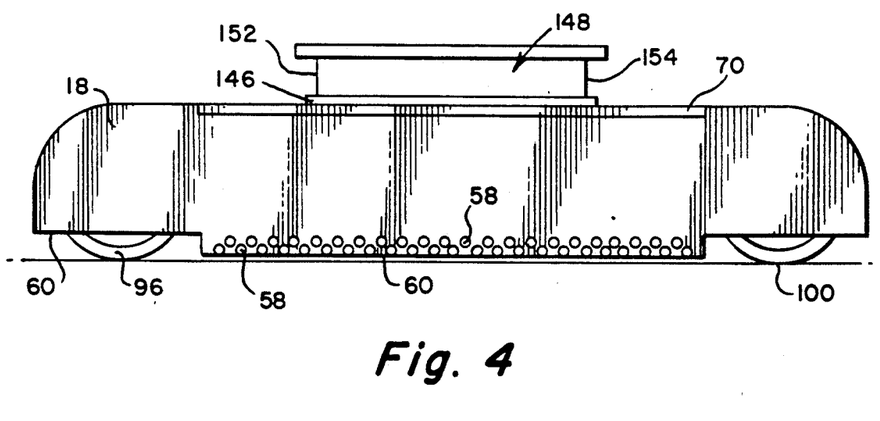
FIG. 4 is a side view of the apparatus means shown in FIG. 1 showing the openings located in a side member thereof through which small magnetic particles may be discharged in dispersed manner onto a wallboard surface.

Extending vertically downwardly from the underside surface of top member 16 are spaced-apart dividing members 34, 36 which are in parallel disposition to one another and laterally disposed relative to the lengthwise direction of elongated body member 12. These dividing members are connected at their end edges 38, 40, 42, 44 to the inner surfaces 46, 48 of respective side members 18, 20 and at their bottom edges 50, 52 to the front and rear edges 54, 56 of bottom member 14, as will be seen in FIG. 2. Although bottom member 14, as is shown in FIG. 3, is connected to the dividing members 34, 36 and side members 18, 20 so that it slants downwardly from one side member to the other, the bottom member need not necessarily be so connected. Nevertheless, such a slant is preferred to ensure that particulate magnetic material, as hereinafter more fully described, is caused to flow toward side member 18, as such is produced during use of the device 10 whereby it will be discharged from the device out through the openings 58 provided in side member 14. As will be seen by reference to FIG. 4, openings 58 are of circular shape and are provided in serial fashion in two rows provided adjacent to the inner portion of bottom edge 60 of side member 18. The end portions of bottom edge 60, as shown in FIG. 4, are located in a plane vertically above that defined by the inner portion. Nevertheless, that need not necessarily be the case. Such end portions can, if desired, be located in the same horizontal plane.

Openings 58 need not be, in all cases, provided in two rows. A single row of such openings will also be found suitable in some cases. The main thing is that the openings be provided near the bottom edge of the side member 18, just above where such side member joins with bottom member 14, so that the particulate magnetic material will be readily discharged from the body member when the stud finding device 10 is being used, as hereinafter more fully disclosed. The size of the openings can vary somewhat. Nevertheless, each should be of such a diameter as to readily allow discharge of particulate material varying in length from about 1/64" to about ⅛". Naturally, such particulate material will have a transverse dimension or diameter of much smaller dimension. Thus, openings 58 about ⅛" diameter should readily accommodate the particulate material whether or not it is expelled through such openings in lengthwise direction.

As earlier stated, bottom member 14 need not necessarily be mounted so as to slant downwardly from one side member to the other, as shown in FIG. 3. Such member can be, if desired, mounted in horizontal disposition. In that case, openings such as shown by reference numeral 58 can be provided in each of the side members 18, 20, requiring less attention in the use of the stud finder device 10, as will be, it is believed, readily appreciated hereinafter. Thus, particulate material can be discharged from either side of the device, as will be later more fully appreciated. The bottom edge of side member 20 will terminate in the same horizontal plane as the bottom edge of side member 18.

The inner edges of central portion 22, 24 of top member 16 extend perpendicularly laterally to the lengthwise direction of device 10 and define an opening for an internal centrally disposed closed cavity 60, the purpose for which will be later explained. As will be appreciated by reference to FIG. 2, the internal cavity 60 is defined by the top surface 62 of bottom member 14, the inner surfaces 64, 66, respectively, of dividing members 34, 36, and the bottom surface 68 of closure member 70, which provides a closure to the internal cavity 60 while at the same time providing access thereto, as needed. Closure member 70 is hinged, in accordance with conventional techniques, at its rear edge 72, making for easy access to cavity 60. Thus, although not shown in the drawings, it will be appreciated that the ends of hinge pin 74 are located in respective side members 18, 20. The front edge 76 of the closure member 70 is located in an elongated notch 78 defined by the inner, lateral edge of central portion 22 and the top surface of the horizontally disposed flange 80 extending perpendicularly outwardly from the top edge of dividing member 34. Thus, as shown in FIG. 2, there is a smooth transition between the top surface of closure member 70 and that of centrally disposed portions 22, 24 of top member 16 whereby all lie in the same horizontal plane. Extending vertically downwardly from the bottom surface 68 of closure member 70, is a rectangular-shaped flange 82 which extends around the side and front edges of the closure member. The outer surfaces of this flange mate with the top inner surfaces of side members 18, 20 and that of dividing member 34 providing a friction fit therewith. Thus, closure member 70 is kept securely engaged in top member 16. Nevertheless, it can be opened when, and as, desired.

Extending between, and supported by, side members 18, 20 in the front and rear cavities 84, 86 are elongated axles 88, 90, 92, 94 which support for rotation, respectively, rubber wheels or rollers 96, 98, 100, 102. These axles are each defined by inner and outer ends and are supported at their outer ends by the respective side members 18, 20 in bearings (not shown) according to usual techniques, whereby on being rotated the rubber rollers will cause rotation of the respective axles. Nevertheless, those in the art will appreciate that, if desired, the axles can be mounted so as to be stationary relative to the side members 18, 20, in which case the rubber rollers 96, 98, 100, 102 will rotate, instead, on their respective axles.

The rollers need not necessarily be of rubber. They can be of any material desired provided such will provide positive traction between the rollers and a wall surface, as later more fully disclosed, in use of the stud and screw finding device 10. The rollers can be of solid rubber, if desired, each on a respective axle of metal, or other suitable material. In some cases, a plastic rod can be used for construction of the axles. Plastic materials conventionally used for such purpose are well known, e.g. Delrin ® polyacetal resin is one example. This plastic material also has low friction characteristics and may, in some cases, be used also for bearing surfaces at the axle ends. If desired, the rollers can be constructed with a core of one material, e.g., plastic or metal, and the peripheral surface of a different material, e.g., rubber.

It will be appreciated by reference to FIG. 2 that the front and rear cavities 84, 86 are defined by the outer surfaces of dividing members 34, 36, the bottom or inner surfaces of central portions 22, 24, and those inner surfaces of end portions 26, 28. Thus, these cavities are open at the bottom thereof so that a portion of the periphery of rollers 96, 98, 100, 102 at the bottom thereof can make contact with a wall surface, such rollers being so mounted that the bottom peripheral surfaces thereof all lie in the same horizontal plane, parallel to that defined by the central portions 22, 24 of top member 16 and that defined by the bottom edges of side member 18, 20. With respect to these bottom edges, however, the horizontal plane defined by the bottom peripheral edges of the rollers must, however, be below that defined by the bottom edges so that, in use, the four rollers will each contact the planar wall surface. See FIG. 2.

The top and bottom members 16, 14 and the side members 18, 20 comprising body member 12 can be provided of various materials as desired, e.g. metal or plastic. Preferably, the body member 12 will be of plastic as such material lends itself to ease, and economies, in manufacture. Thus, a unitary structure comprising the top and bottom members, and the dividing members can be readily manufactured by conventional plastic molding techniques, e.g. injection molding. Various plastic materials conventionally used will be found suitable in the manufacture of body member 12, e.g., acrylics, polyvinyl chloride, polyethylene, ABS resins, nylon, etc. These materials can be compounded with various fillers, plasticizers, coloring agents, etc., according to usual techniques, to provide various properties, as desired. Such manner of manufacture also lends itself to providing the opening in top member 16 for internal cavity 60, during manufacture. Nevertheless, if desired, the various members can be provided as separate components and then connected together by suitable fastening means, e.g. adhesive or fusion bonding, depending upon the particular plastic material being used.

Figure 1:
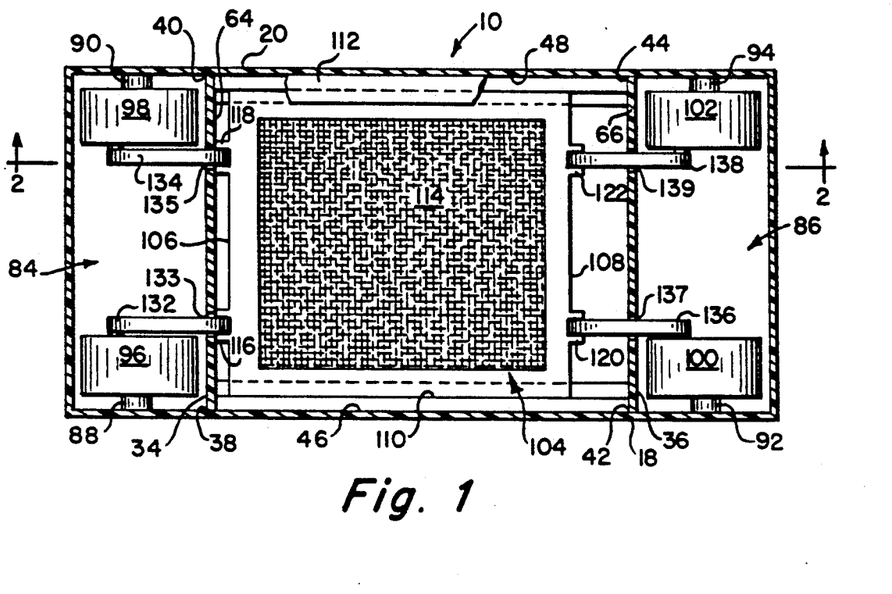
FIG. 1 is a top view in section taken at secant lines 1—1 in FIG. 2 of one apparatus means according to the invention for locating the metal screws which fasten a wallboard member to one or more metal studs,, and the metal studs themselves which are located behind such a partition wall and are hidden from view.

Located within the closed cavity 60 is a horizontally disposed, rectangular-shaped member 104 defined by front and back edges 106, 108 and side edges 110, 112. These edges define a rigid frame work for holding foraminous member 114 which can be connected thereto by various conventional means, depending somewhat upon the particular materials of construction. For example, if desired, the framework can be of metal and the foraminous member 114 of plastic, in which case the foraminous member 114 can be frictionally engaged with the framework or secured thereto by fastening members, e.g. rivets or adhesive. Also, if desired, the member 104 can be provided of unitary construction, e.g. by plastic molding. In this case, the frame or edges can be of a solid plastic material and the central portion be provided with openings or perforations of suitable size, as desired. Such openings can be square as best seen in FIG. 1, like screen-wire, or of other shape, e.g. circular, as desired. The openings should be from about $\frac{1}{8}''-\frac{1}{4}''$ in their greater dimension to let the particulate material, as earlier disclosed, to readily pass through such openings and to drop to the top surface of bottom member 14.

Extending perpendicularly outwardly from the front and back edges 106, 108 of member 104 and in the same horizontal plane therewith are U-shaped lugs 116, 118, 120, 122 through each arm of which is provided a horizontally disposed opening as designated by reference numerals 124, 126 in FIG. 2. Similar openings, not shown, are provided in lugs 118, 122. In each of such openings is located an elongated connector pin, such being indicated in general by reference numerals 128, 130, which connects the inner ends of elongated arms 132, 134, 136, 138 to the horizontally disposed member 104. It will be appreciated, though not specifically shown in the drawing, that arms 132, 134, 136, 138 are each provided with openings at their ends through which the connector pins pass. These arms extend, respectively, through openings 133, 135, 137, 139 provided in dividing members 34, 36, into respective front and rear cavities 84, 86. The other ends of the arms 132, 134, 136, 138, i.e., the outer ends, are pivotally connected in conventional fashion to respective rollers 96, 98, 100, 102 at points offset from the axis of the rollers, as will be appreciated by reference to FIG. 1. Thus, when the rollers are rotated, this circular motion will cause the arms 132, 134, 136, 138 to move back and forth in a horizontal motion and, hence, member 104 to be reciprocated back and forth in a horizontal direction. The action is somewhat like that of the wheels on an old steam locomotive. Referring to FIG. 3, it will be seen that the side edges 110, 112 of member 104 are located, respectively, in horizontally disposed U-shaped guide members 140, 142 located on the inside surfaces of side members 18, 20 and extending outwardly therefrom. Thus, the motion of member 104 will necessarily be back and forth in a horizontal plane.

In closure member 70 there is provided a centrally disposed opening 144 defined by a raised edge 146 which extends vertically upwardly from the top surface of the closure member and defines a square-shaped opening. Nevertheless, the shape of this opening is of no consequence and, in and of itself, forms no particular part of the invention. Extending through opening 144 is a member 148 defined by an elongated, vertically disposed, rectangular-shaped body member 150 and horizontally disposed top and bottom members 152, 154 in parallel disposition to one another. These end members are of slightly larger dimension than opening 144 and one of such end members, at least, is detachably connected to body member 150 so that member 148 can be located in the opening 144. Such end member is then reattached to the body member, e.g. friction fitted. The dimensions of body member 150 are slightly less than those of opening 144 so that member 148 is free to float, or move vertically up and down in the opening 144 for a reason soon to be disclosed. Nevertheless, in some cases, it may be desirable to provide that body member 150 be tapered inwardly from top to bottom. Thus, as member 148 is pushed downwardly into cavity 60, the body member 148 will become frictionally engaged with the edges of opening 144. In this case, the bearing or bottom surface 158 of bottom member 154 will be firmly seated against the top surface of the steel wool pad 156, as hereinafter more fully disclosed.

In anticipation of use, closure member 70 is opened, by taking a hold of member 148 with one hand while holding body member 12 with the other and pulling on member 148. Then, a conventional steel wool pad 156 is located within the internal cavity 60, as shown in FIG. 2 with its bottom surface resting on the top surface of foraminous member 114. Next, closure member 70 is closed and floating member 148 is pushed vertically downwardly against the top surface of the steel wool pad 156. Thus, bottom planar surface 158 of member 150 and top planar surface 160 of foraminous member 114 provide parallel bearing surfaces which bear against and hold the steel wool pad horizontally in place. The extent of the forces bearing against the steel wool pad 156 can be more or less, depending on how much one pushes downwardly on the floating member 150. If desired, to ensure that the steel wool pad remains in place one can provide spikes such as indicated by reference numeral 159, e.g. about $\frac{1}{8}$" long, on the bearing surface 158 extending perpendicular thereto and outwardly therefrom. Thus, the steel wool pad 156 can be maintained in place while its bottom is being abraded away into particles.

Figure 5:
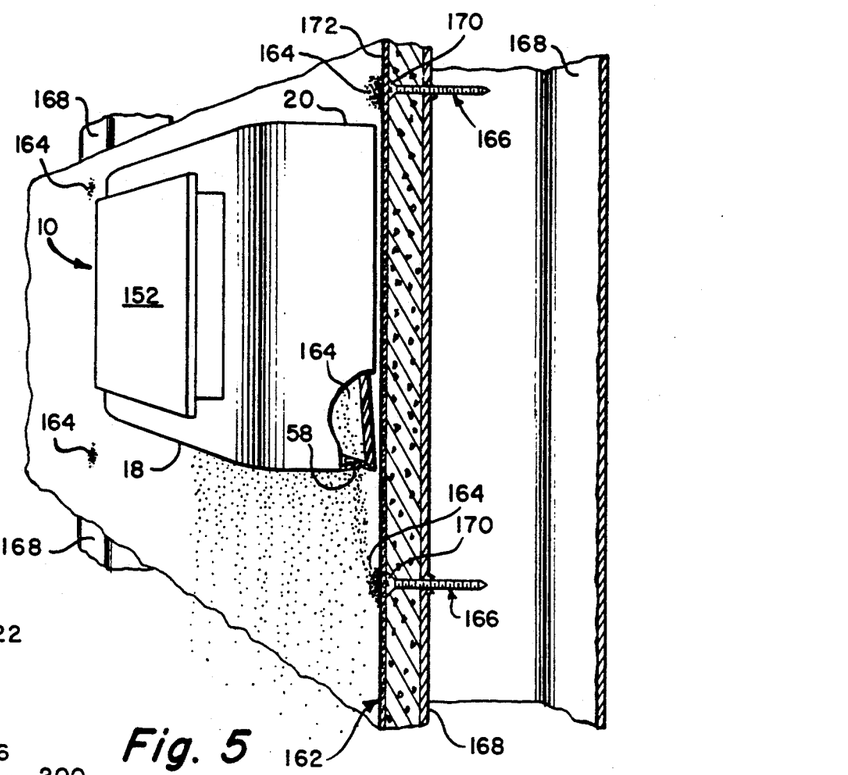
FIG. 5 is a view in perspective showing the outside surface of a wall behind which are located vertically upright metal studs, and showing magnetic particles being discharged from the apparatus means shown in FIG. 1 and dispersed onto such surface and then being attracted to the heads of the metal screws which are located in the metal studs and which fasten the wallboard to the studs.

In use, the stud and screw finding device 10 is positioned against the surface of a wall 162 (FIG. 5) adjacent the ceiling such that the bottoms of the rubber rollers contact such surface and the axles of such rollers are disposed in vertically upright position. Thus, side members 18, 20 will be disposed in horizontal fashion relative to and parallel to the ceiling. If openings 58 are provided in only one of the side members, that side member provided with such openings should be facing toward the floor, the reason for such being soon made clear. Starting at one vertical edge of the wall, the stud finding device 10 is moved horizontally toward the other vertical edge of the wall in such a fashion that it is always maintained in horizontal disposition. As the horizontal movement continues, the rotation of the rollers translates into a reciprocal action of the foraminous member 114 and in back and forth horizontal movement. This reciprocal movement of the foraminous member against the steel wool pad 156 causes small particles 164 of steel wool to be shredded from the outer bottom surface of the pad. These small steel wool particles 164 drop downwardly as they are formed onto the bottom member 14 and such particles fall outwardly through the openings 58 provided in the side member 18. These particles being iron are magnetic, i.e., they are attracted to the field of force of a magnet. Thus, as these steel wool particles 164 fall freely vertically downwardly along the wall surface 162, such are attracted by the fields of force of the magnetized screws 166 located in the metal studs 168. Thus, the resulting clumps or clusters of magnetic particles define the location of the head 170 of each screw 166 and, in turn, the metal studs 168. The magnetic particles 164 are attracted to the heads 170 of the screws 166 even though such are located behind spackling compound 172 or other materials conventionally used to cover over the screw heads 170 in finishing the wall surface. Thus, such screw heads, though hidden from view, can be readily located by my invention as disclosed herein. And, once the location of the screw-type fasteners 166 is determined, the location of the metal stud 168 in which such fasteners are located can be readily determined also. As will be readily appreciated, the screw-heads, hence the metal stud behind such, will be identified by the spaced-apart vertically disposed clusters of magnetic particles, as shown in FIG. 5.

When using the stud finder device 10 according to this embodiment of the invention, one will ordinarily grasp hold of such by taking a hold of the side members 18, 20 between one's thumb and fingers with the palm against end member 152. Thus, such action causes a downward force to be registered against member 148 which is free to move up and down, and bearing surface 158 to be pressed against the steel wool pad 156. In turn, this causes the bottom surface of steel wool pad 156 to be pressed against the upper or bearing surface 160 of the foraminous member 114. Thus, this surface being a foraminous member acts to abrade small particles from the steel wool pad, or at least to cause it to be shredded or to disintegrate into small particles, varying in size from about 1/64" to about $\frac{1}{8}$" in length, as the foraminous member is reciprocated in back and forth motion.

The foraminous member 114 can, if desired, be made somewhat more abrasive by making such openings sharp, e.g. by providing vertically disposed rough edges, much like a grater commonly used in the kitchen. Or abrasive material, i.e., abrasive grains can be provided on the bearing surface 160.

Although not shown in the drawing, in an alternative embodiment a spring member can be located within cavity 60 to maintain the steel wool pad 156 in place, while such is being abraded. Such a spring member can take various shapes and constructions as will be readily appreciated by those skilled in the art, e.g. two elongated, laterally spaced-apart, coiled springs fastened at their respective ends by hooks attached to the inner surfaces of dividing members 34, 36. Thus, the springs will be unhooked at their one end, the pad located on the foraminous member, and the springs then rehooked. Or the spring can be like that provided in a rat or mouse trap, the spring being mounted on the inside surface of dividing member 36 so that such is always biased toward the top surface of the foraminous member. With such a spring member, member 148 need not be provided. Accordingly, opening 60 need not be provided, in such an embodiment, in the closure member.

Although the use of the stud finder device 10, as above disclosed, involves locating all the metal studs behind a wallboard member, and the screw-type fasteners holding such to the studs, it can obviously be used just to locate one stud, if such is desired. Thus, rather than positioning the device on the wall at the ceiling, adjacent an edge or corner of a room, device 10 can be positioned adjacent where, e.g., one wants to locate a stud to use as a foundation to hang a picture. With the device oriented, as shown in FIG. 5, the stud finding device is moved horizontally in back and forth direction about 24–30 inches. As the magnetic particles fall freely toward the floor such will be attracted by the magnetic force associated with each of the screw-type fasteners located in that particular stud. Locating at least two of such fasteners will allow determination of the location of the stud, as two points determine a straight line. The more hidden screws located, however, the more accurate will that determination be.

Figure 6:
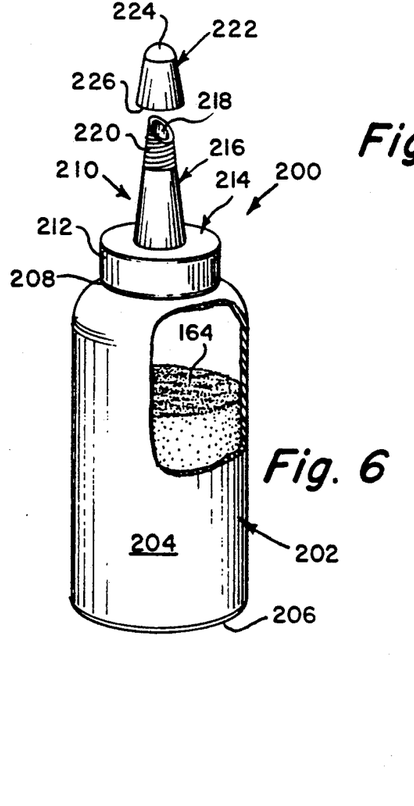
FIG. 6 is a view in perspective, in partial section, of another more simple, apparatus means according to the invention for locating hidden metal wall studs and the metal screws driven therein for fastening the wallboard members to the studs.

Turning now to FIG. 6 of the drawing there is shown another, though somewhat less preferred stud finding device 200 according to the broadest aspects of the concept of my invention. As shown therein, the stud finding device 200 comprises a container having a body member 202 defined by a cylindrical shaped elongated outer upright wall member 204 closed at its bottom end 206 and open at its top end 208. The opening at the top end (not shown) is defined in usual fashion by a circular-shaped mouth or lip provided with external screw threads (not shown). Detachably connected to the body member 202 at its open end is a spout member 210 which is defined by a cylindrical-shaped base member 212 having an open bottom end with a thread pattern (not shown) provided on its inside surface complementary to the thread pattern provided on the mouth of the body member 202. Extending vertically upwardly from the top end of the base member 212 and centrally disposed in annular shaped end member 214 is an elongated spout 216 which tapers inwardly from its circular-shaped base and terminates in an open end 218. The spout is provided with a thread pattern 220 on its outside surface at its open end for connection of the cone-shaped end cap 222, which, as will be appreciated, is closed at its outer end 224 and open at its inner end 226. End cap 222, though not shown, is provided with a thread pattern on its inside surface complementary to thread pattern 220.

Located within body member 202 is a mass of loose magnetic particles 164, e.g. iron filings or shredded steel wool, having a length of from about 1/64" to about $\frac{1}{8}$". These particles, as shown in FIG. 6, and this is a critical aspect of the invention, must not take up the entire volume of the container, e.g. no more than about $\frac{2}{3}$ of the available volume, as shown in FIG. 6, when the container is initially filled with the magnetic particles. However, this will depend somewhat upon the size, e.g., the diameter of the body member 202. Otherwise, the body member 202 may contain an insufficient amount of air therein with which to initially expel the magnetic particles out the spout 216. It will be appreciated that, dependant somewhat upon the volume of the body member, more or less air in the body member along with the mass of magnetic particles will provide the most optimum expulsion characteristics, initially. As the magnetic particles are expelled from the body member during use, an ever increasing volume becomes available for air, providing a ready amount of air for expulsion of the remaining particles.

The body member 202 need not be of cylindrical shape; however, such a shape is most preferred, as such shape can be more readily grasped in one's hand. This member can be square-shaped, if desired. The main thing is that the walls 204 of the body member be sufficiently flexible to allow the body member to be squeezed whereby air is expelled through the spout, carrying with it particulate material. When the squeezing force is released, air will then be pulled into the internal cavity formed by the body member and occupy the space not being then occupied by the magnetic particles.

To use the stud finding device 200, in finding all the hidden metal studs behind a wallboard member, the end cap 222 is first removed from the end of the elongated spout 216 The device is then positioned about 6" below the ceiling and about 24" from the left vertical edge of the wall with the open spout end facing towards the wall surface. The body member is then given repeated squeezes while causing such to move in a horizontal direction from left to right from the one corner of the room to the other. As short spurts of the particulate, magnetic material are expelled from the spout onto and against the wall surface, such particles fall freely toward the floor and are dispersed over the wall surface. The particles are seen to accumulate and form clusters around an area on the wall surface behind which is located the head of a screw-type fastener 166, as shown in FIG. 5. The procedure may be repeated one or more times to locate addition fasteners by starting again at the same corner of the room, at a point each time somewhat lower vertically downwardly from the ceiling. As will be appreciated, the horizontal movement may be from right to left, if desired, rather than from left to right.

The foregoing detailed description has been given for clearness of understanding only and no unnecessary limitations are to be understood therefrom. The invention is not limited to the exact details shown and described for obvious modifications and variations will now occur to those skilled in the art without departing from the spirit and scope of the invention as described in the following claims.

What I claim is:

1. Method for locating a plurality of metal studs disposed in upright manner and spaced apart from one another horizontally along a wall, said metal studs being hidden from view by a vertically disposed wallboard member having a front face facing outwardly into a room or other open area and being defined by vertically upright first and second edges, said wallboard member being secured to each of the said plurality of metal studs by a plurality of spaced-apart metal screw-type fasteners located in vertical disposition along each said metal stud, said crew-type fasteners being characterized by their ability to attract magnetic particles comprising the following steps:
   (a) providing in loose fashion particulate magnetic material capable of being attracted by said fasteners; and
   (b) causing said particulate material to be deposited in dispersed manner on the said front surface of the wallboard member between said upright edges whereby a portion of said particulate material is attracted to one of the said screw-type fasteners, and other portions of the particulate material will be attracted to other of said fasteners; and whereby the location of said studs is thereby defined.

2. Method for locating a plurality of metal studs according to claim 1 wherein said particulate material is provided in a container for containing said particulate material in loose fashion, said container being provided with spout means through which said particulate material can be expelled onto the outer surface of said wall member.

3. Method for locating a plurality of metal studs according to claim 2 wherein said particulate material is caused to be deposited on the said front surface of the wall panel by expelling said particles from the container while moving such across the wallboard member in horizontal fashion while at the same time moving from the said first vertically upright edge to the said second vertically upright edge.

4. Method for locating a plurality of metal studs according to claim 3 wherein the said particulate material is expelled against the wallboard panel adjacent the first named vertically disposed edge and adjacent the ceiling defining the said room or other area, said expelled particulate material being allowed to fall freely toward the floor defined by the said room or other area while at the same time being attracted by the magnetic field defined by each of said screw-type fasteners whereby particulate material in being attracted to a screw type fastener associate themselves with and define the location of a fastener.

5. Method for locating a plurality of metal studs according to claim 3 wherein said particulate material is provided by causing a steel wool pad to be shredded into particles of the desired size.

6. Method for locating a plurality of metal studs according to claim 5 wherein a foraminous member is reciprocated back and forth against the steel wool pad to abrade it into said particles.

7. Method for locating a plurality of metal studs according to claim 1 wherein said particulate magnetic material is provided in lengths from about 1/64" to about ⅛".

8. Method for locating a plurality of metal studs according to claim 2 wherein the volume of said particulate material provided in the container is less than the available volume of the container and a sufficient amount of air is provided in the container to cause the particulate material to be expelled therefrom.

* * * * *

UNITED STATES PATENT AND TRADEMARK OFFICE
CERTIFICATE OF CORRECTION

PATENT NO. : 5,296,806

DATED : March 22, 1994

INVENTOR(S) : Charles J. Hurl, Jr.

It is certified that error appears in the above-identified patent and that said Letters Patent is hereby corrected as shown below:

Claim 1, column 12, line 42, the word "crew-type" should read --screw-type--.

Claim 5, column 13, line 17, the words "claim 3" should read --claim 1--.

Signed and Sealed this

Twenty-sixth Day of July, 1994

Attest:

BRUCE LEHMAN

Attesting Officer

Commissioner of Patents and Trademarks